(12) United States Patent
Takeda et al.

(10) Patent No.: US 9,957,241 B2
(45) Date of Patent: May 1, 2018

(54) AROMATIC DIAMINE, AN INTERMEDIATE THEREFOR, A METHOD FOR PRODUCING THE AROMATIC DIAMINE, AND A METHOD FOR PRODUCING THE INTERMEDIATE THEREFOR

(71) Applicant: SEIKA CORPORATION, Wakayama, Wakayama (JP)

(72) Inventors: Motonori Takeda, Wakayama (JP); Masahiro Kasamatsu, Wakayama (JP); Akihiro Tamaki, Wakayama (JP); Seiichi Mori, Wakayama (JP); Mitsutaka Imoto, Wakayama (JP); Yoshihisa Takeda, Wakayama (JP)

(73) Assignee: SEIKA CORPORATION, Wakayama (JP)

( * ) Notice: Subject to any disclaimer, the term of this patent is extended or adjusted under 35 U.S.C. 154(b) by 0 days. days.

(21) Appl. No.: 15/562,162

(22) PCT Filed: Mar. 29, 2016

(86) PCT No.: PCT/JP2016/060030
§ 371 (c)(1),
(2) Date: Sep. 27, 2017

(87) PCT Pub. No.: WO2016/158907
PCT Pub. Date: Oct. 6, 2016

(65) Prior Publication Data
US 2018/0079732 A1    Mar. 22, 2018

(30) Foreign Application Priority Data

Mar. 31, 2015 (JP) ................................ 2015-073538
May 26, 2015 (JP) ................................ 2015-106275

(51) Int. Cl.
*C07D 277/66* (2006.01)
*C07D 263/57* (2006.01)

(52) U.S. Cl.
CPC ......... *C07D 277/66* (2013.01); *C07D 263/57* (2013.01)

(58) Field of Classification Search
CPC ............................ C07D 277/66; C07D 263/57
See application file for complete search history.

(56) References Cited

U.S. PATENT DOCUMENTS

| 5,567,800 A | 10/1996 | Hergenrother et al. |
| 6,281,323 B1 | 8/2001 | Yokota et al. |

FOREIGN PATENT DOCUMENTS

| JP | 2000-219741 A | 8/2000 |
| JP | 2006-104440 A | 4/2006 |
| JP | 2011-1279 A | 1/2011 |
| WO | 2003/074515 A1 | 9/2003 |
| WO | 2003/074516 A1 | 9/2003 |
| WO | 2007/09116 A1 | 1/2007 |

OTHER PUBLICATIONS

Jun. 28, 2016 Search Report issued in International Patent Application No. PCT/JP2016/060030.
Jun. 28, 2016 Written Opinion issued in International Patent Application No. PCT/JP2016/060030.
"Recent Polyimide, Fundamentals and Applications", edited by Japan Polyimide and Aromatic Polymer Conference, pp. 222-230.
Rikio Yokota, "Polyimide and Aromatic Polymer", Recent Progress 2013, pp. 20-25.
Chen, J. et al., "Novel Polyimides Containing Benzimidazole for Temperature Proton Exchange Membrane Fuel" Journal of Membrane Science, (Feb. 28, 2015), vol. 483, pp. 144-154.
Toiserkani, H., "Modified Poly (Ether-Imide-Amide)S With Pendent Benzazole Structures: Synthesis and Characterization", Journal of Applied Polymer Science, 2012, vol. 125 (2), pp. 1576-1585.
Toiserkani, H. et al., "New Organosoluble and Thermally Stable Poly(Amide-Imide)S With Benzoxazole or Benzothiazole Pendent Groups: Synthesis and Characterization", Polymers Advanced Technologies, (2011), vol. 22 (11), pp. 1494-1501.
Richardson, T. O. et al., "Synthesis of 7-Benzoxazol-2-Yl and 7-Benzthiazol-2-Yl-6-Fluoro-Quinolones", Journal of Heterocyclic Chemistry, (1998), vol. 35(6), pp. 1301-1304.

*Primary Examiner* — Laura L. Stockton
(74) *Attorney, Agent, or Firm* — Oliff PLC

(57) ABSTRACT

A novel asymmetric diamine, diamino-2-(benzothiazole-2-yl)diphenyl ether, derivatives therefor, and an intermediate for the compound such as aminonitro-2-(benzothiazole-2-yl)diphenyl ether, dinitro-2-(benzothiazole-2-yl)diphenyl ether, and derivatives from these. Additionally, another novel asymmetric diamine, diamino-2-(benzoxazole-2-yl) diphenyl ether, derivatives therefor, and intermediate for the compound such as aminonitro-2-(benzoxazole-2-yl)diphenyl ether, dinitro-2-(benzoxazole-2-yl)diphenyl ether, and derivatives from these, and methods for preparing them.

5 Claims, 6 Drawing Sheets

AROMATIC DIAMINE, AN INTERMEDIATE THEREFOR, A METHOD FOR PRODUCING THE AROMATIC DIAMINE, AND A METHOD FOR PRODUCING THE INTERMEDIATE THEREFOR

FIELD OF THE INVENTION

The present invention relates to diamino-2-(benzothiazole-2-yl)diphenyl ether, derivatives therefor, diamino-2-(benzoxazole-2-yl)diphenyl ether, derivatives therefrom, and methods for preparing them. These compounds are useful as raw materials for highly functional polymers including polyimides, and various organic compounds. The present invention further relates to an intermediate for diamino-2-(benzothiazole-2-yl)diphenyl ether, such as aminonitro-2-(benzothiazole-2-yl)diphenyl ether, dinitro-2-(benzothiazole-2-yl)diphenyl ether and derivatives from these, an intermediate for diamino-2-(benzoxazole-2-yl)diphenyl ether such as aminonitro-2-(benzoxazole-2-yl)diphenyl ether, dinitro-2-(benzoxazole-2-yl)diphenyl ether, and derivatives from these, and methods for preparing them.

BACKGROUND OF THE INVENTION

Recently, polymer materials have been desired which have high heat resistance, high tenacity in extreme conditions such as in cosmic space, and easy moldability. Patent Literature 1 describes a method of attaining high heat resistance in molding without generating volatile components by heat curing while maintaining good processability wherein a polyimide oligomer is heated and capped with a capping agent such as phenylethynylphthalic anhydride, molded, heated and, then, crosslinked and cured at the phenylethynyl group. Patent Literature 2 discloses a method for improving flowability and processability of an oligomer using asymmetric tetracarboxylic anhydride in the preparation of a composite of carbon fiber and polyimide. A cardo-type diamine is used in Patent Literature 3. The asymmetric diamine disclosed in Patent Literature 4 is 2-(4-aminophenoxy)-5-aminobiphenyl.

In particular, 2-(4-aminophenoxy)-5-aminobiphenyl described in Patent Literature 4 is a raw material for preparing a polymer having high heat resistance, high tenacity and easy moldability and broadens the potentiality of asymmetric polyimides (Non-Patent Literature 1). Non-Patent Literature 2 describes that many of asymmetric polyimides have a high melt flowability on account of active segmental movement at a temperature higher than a glass-transition temperature. Therefore, further asymmetric diamines are desired to be used as a raw material of asymmetric polyimides.

PRIOR LITERATURES

Patent Literatures

[Patent Literature 1] U.S. Pat. No. 5,567,800
[Patent Literature 2] Japanese Patent Application Laid-Open No. 2000-219741
[Patent Literature 3] Japanese Patent Application Laid-Open No. 2006-104440
[Patent Literature 4] Japanese Patent Application Laid-Open No. 2011-1279

Non-Patent Literatures

[Non-patent Literature 1] Recent Polyimide, Fundamentals and Applications, edited by Japan Polyimide and Aromatic Polymer Conference, pages 222 to 230
[Non-Patent Literature 2] Polyimide and Aromatic Polymer, Recent Progress 2013, edited by Rikio Yokota, pages 20 to 25

SUMMARY OF THE INVENTION

Problems to be Solved by the Invention

Accordingly, one of the purposes of the present invention is to provide an asymmetric diamine suitable for preparing a soluble polyimide and a method for preparing the same.

Means to Solve the Problems

To solve the aforesaid problems, the present inventors have made research and developed novel asymmetric diamines which are diamino-2-(benzothiazole-2-yl)diphenyl ether, derivatives therefrom and intermediates for diamino-2-(benzothiazole-2-yl)diphenyl ether, i.e., aminonitro-2-(benzothiazole-2-yl)diphenyl ether, dinitro-2-(benzothiazole-2-yl)diphenyl ether, and derivatives from these. The present inventors have further developed other novel asymmetric diamines, i.e., diamino-2-(benzoxazole-2-yl)diphenyl ether, derivatives therefrom, and intermediates for diamino-2-(benzoxazole-2-yl)diphenyl ether, i.e., aminonitro-2-(benzoxazole-2-yl)diphenyl ether, dinitro-2-(benzoxazole-2-yl)diphenyl ether, and derivatives of these. The present inventors have further found that diamino-2-(benzothiazole-2-yl)diphenyl ether, derivatives thereof, diamino-2-(benzoxazole-2-yl)diphenyl ether and derivatives thereof have good properties comparable to the properties of 2-(4-aminophenoxy)-5-aminobiphenyl and that these compounds are easily prepared.

Thus, the present invention provides a compound represented by the following formula (1):

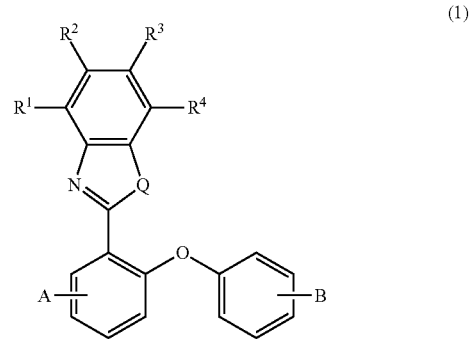

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, A and B are, independently of each other, a nitro group or an amino group, and Q is an oxygen atom or a sulfur atom.

The present invention further provides a method for preparing a compound represented by the following formula (1-e):

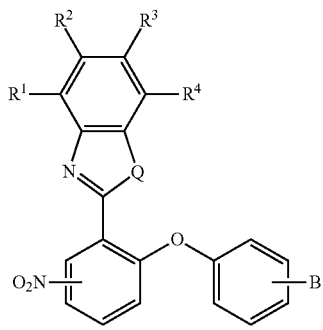

(1-e)

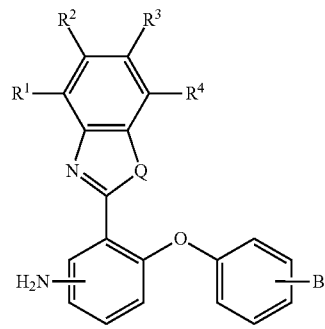

(1-f)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, B is a nitro group or an amino group, and Q is an oxygen atom or a sulfur atom, wherein the method comprises a step of reacting a nitrophenyl benzothiazole or nitrophenyl benzoxazole compound represented by the following formula (2):

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, B is a nitro group or an amino group, and Q is an oxygen atom or a sulfur atom, wherein the method comprises a step of reacting an aminophenyl benzothiazole or aminophenyl benzoxazole compound represented by the following formula (4):

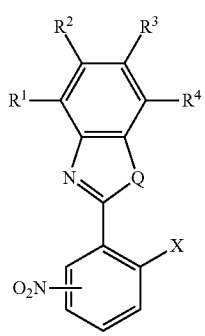

(2)

(4)

wherein Q, $R^1$, $R^2$, $R^3$ and $R^4$ are as defined above and X is a halogen atom, with a phenol compound represented by the following formula (3) or a metal salt of the phenol compound:

wherein Q, $R^1$, $R^2$, $R^3$ and $R^4$ are as defined above and X is a halogen atom, with a phenol compound represented by the following formula (3) or a metal salt of the phenol compound:

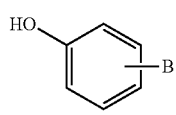

(3)

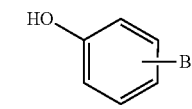

(3)

wherein B is a nitro group or an amino group, to thereby prepare the compound represented by the aforesaid formula (1-e).

The present invention further provides a method for preparing a compound represented by the following formula (1-f):

wherein B is a nitro group or an amino group, to thereby prepare the compound represented by the aforesaid formula (1-f).

The present invention further provides a method for preparing a compound represented by the following formula (1-a):

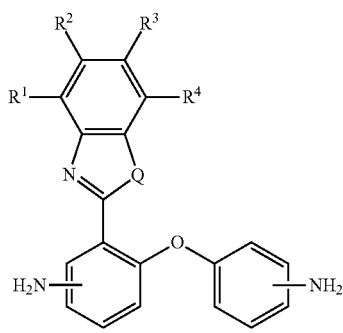

(1-a)

wherein R¹, R², R³ and R⁴ are, independently of each other, a hydrogen atom, an alkyl group having 1 to 6 carbon atoms, or an alkoxy group having 1 to 3 carbon atoms, and Q is an oxygen atom or a sulfur atom, wherein the method comprises a step of reducing a nitro group of a compound represented by the following formula (1-e) or (1-d) to thereby prepare the compound represented by the aforesaid formula (1-a),

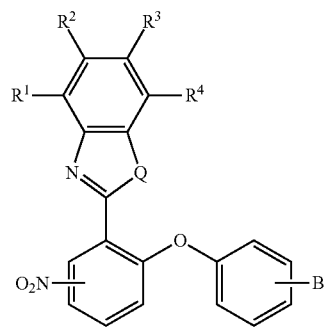

(1-e)

wherein Q, R¹, R², R³ and R⁴ are as defined above and B is a nitro group or an amino group,

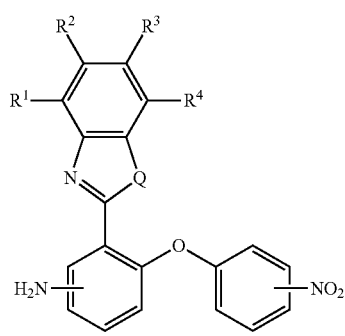

(1-d)

wherein Q, R¹, R², R³ and R⁴ are as defined above.

Effects of the Invention

Diamino-2-(benzothiazole-2-yl)diphenyl ether and its derivatives, and diamino-2-(benzoxazole-2-yl)diphenyl ether and its derivatives can be suitably used as an asymmetric diamine, broaden the potentiality of the field of polyimides derived from the compounds and provide new functional materials.

BRIEF EXPLANATION OF THE DRAWINGS

FIG. 1-2 is a chart of $^{13}$C-NMR spectra of the compound prepared in Example 1-2.

FIG. 2-1 is a chart of $^1$H-NMR spectra of the compound prepared in Example 2-2.

FIG. 2-2 is a chart of $^{13}$C-NMR spectra of the compound prepared in Example 2-2.

FIG. 2-3 is a chart of $^1$H-NMR spectra of the compound prepared in Example 2-4.

FIG. 2-4 is a chart of $^{13}$C-NMR spectra of the compound prepared in Example 2-4.

DETAILED DESCRIPTION OF THE INVENTION

Figure 1:
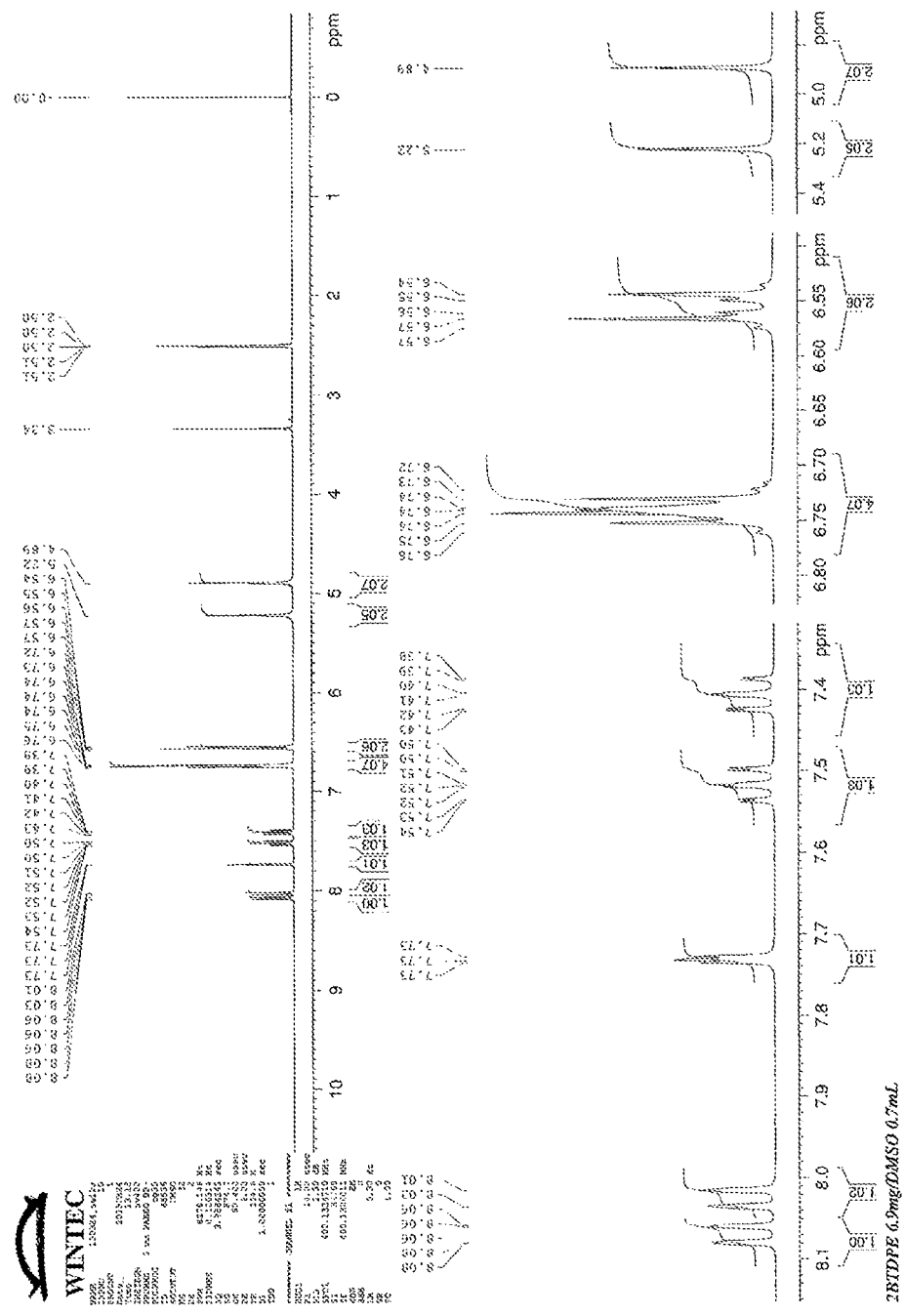
FIG. 1-1 is a chart of $^1$H-NMR spectra of the compound prepared in Example 1-2.

The compound wherein Q is a sulfur atom in the aforesaid formula (1) is a benzothiazole-2-yl-diphenyl ether which has an amino group and/or a nitro group and is represented by the following formula (1-1). This compound is referred to as compound 1 in the present specification.

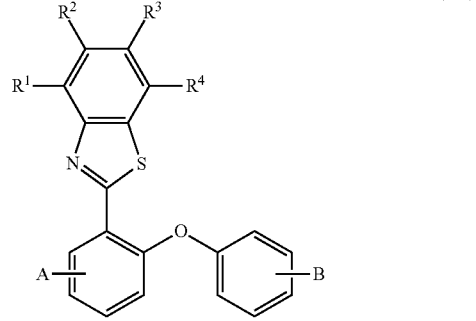

(1-1)

wherein R¹, R², R³ and R⁴ are, independently of each other, a hydrogen atom, an alkyl group having 1 to 6 carbon atoms, or an alkoxy group having 1 to 3 carbon atoms, and A and B are, independently of each other, a nitro group or an amino group.

The compound wherein Q is an oxygen atom in the aforesaid formula (1) is a benzoxazole-2-yl-diphenyl ether which has an amino group and/or a nitro group and is represented by the following formula (2-1). This compound is referred to as compound 2 in the present specification.

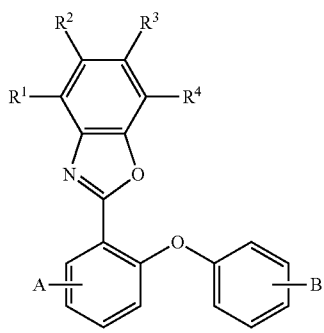

(2-1)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group.

The present compounds 1 and 2 will be described below in detail.

[Compound 1]

Compound 1 is a benzothiazole-2-yl-diphenyl ether or its derivatives, which have an amino group and/or a nitro group and are represented by the following formula (1-1).

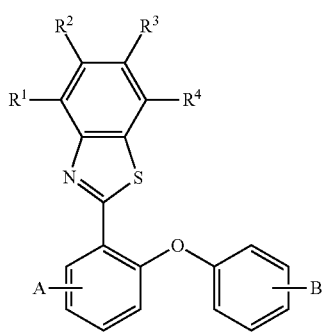

(1-1)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group.

In the aforesaid formula (1-1), A is bonded to one of the carbon atoms at position 3, 4, 5 or 6 in the benzene ring. B is bonded to one of the carbon atoms at position 2', 3' or 4' in the benzene ring. The positions in the benzene ring are illustrated below.

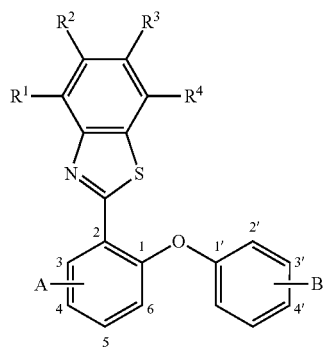

In the formula (1-1), $R^1$, $R^2$, $R^3$ and $R^4$ may be a branched alkyl group having 1 to 6 carbon atoms. Examples of the alkyl group include a methyl group, an ethyl group, a propyl group, an isopropyl group, a butyl group, a pentyl group, and a hexyl group. Among these, an alkyl group having 1 to 3 carbon atoms is preferable. Examples of the alkoxy group having 1 to 3 carbon atoms include a methoxy group, an ethoxy group, a propoxy group, and an isopropoxy group. In particular, $R^1$, $R^2$, $R^3$ and $R^4$ are, independently of each other, a hydrogen atom or an alkyl group having 1 to 3 carbon atoms, further preferably a hydrogen atom.

The compound wherein A and B are both an amino group in the formula (1-1) is represented by the formula (1-1-a) and is diamino-2-(benzothiazole-2-yl)diphenyl ether or its derivatives.

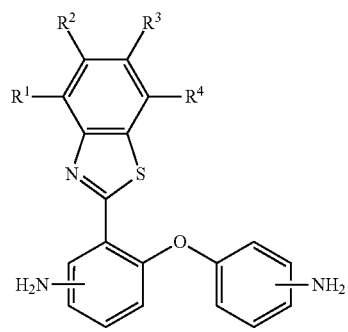

(1-1-a)

wherein $R^1$, $R^2$, $R^3$ and $R^4$ are as defined above.

The compound represented by the formula (1-1-a) is preferably one represented by the following formula.

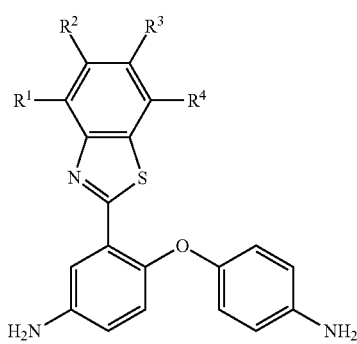

wherein $R^1$, $R^2$, $R^3$ and $R^4$ are as defined above. In particular, $R^1$, $R^2$, $R^3$ and $R^4$ are, independently of each other, a hydrogen atom or an alkyl group having 1 to 3 carbon atoms, further preferably a hydrogen atom.

The compound whose A and B in the formula (1-1) are both an nitro group is represented by the following formula (1-1-b) and is dinitro-2-(benzothiazole-2-yl)diphenyl ether and its derivatives. This compound may be used as an intermediate for the aforesaid diamino-2-(benzothiazole-2-yl)diphenyl ether or its derivatives, which are represented by the formula (1-1-a).

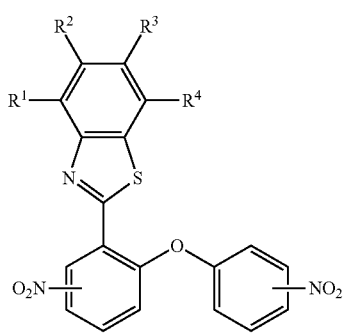

(1-1-b)

wherein $R^1$, $R^2$, $R^3$ and $R^4$ are as defined above.

The compound wherein one of A and B in the formula (1-1) is an amino group and the other is an nitro group is represented by the following formula (1-1-c) or (1-1-d) and is aminonitro-2-(benzothiazole-2-yl)diphenyl ether or its derivatives. This compound may be used as an intermediate for the aforesaid diamino-2-(benzothiazole-2-yl)diphenyl ether or its derivatives, which are represented by the formula (1-1-a).

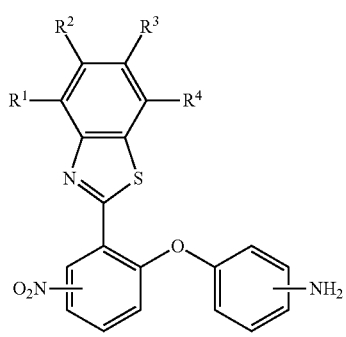

(1-1-c)

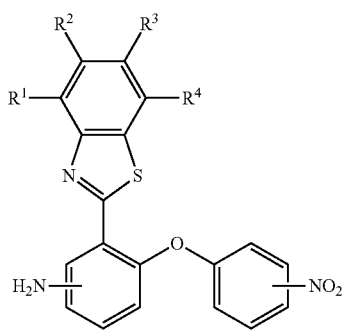

(1-1-d)

wherein $R^1$, $R^2$, $R^3$ and $R^4$ are as defined above.

[Compound 2]

Compound 2 is a benzoxazole-2-yl-diphenyl ether or its derivatives, which has an amino group and/or a nitro group and is represented by the following formula (2-1).

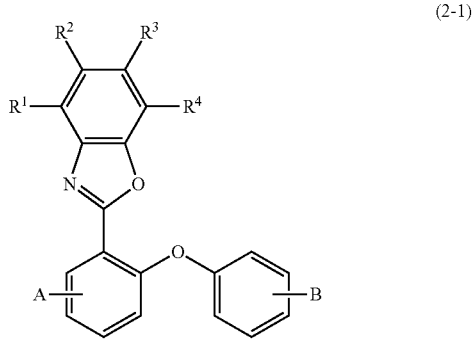

(2-1)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and A and B are, independently of each other, a nitro group or an amino group.

In the aforesaid formula (2-1), A is bonded to one of the carbon atoms at position 3, 4, 5 or 6 in the benzene ring. B is bonded to one of the carbon atoms at position 2', 3' or 4' in the benzene ring. The positions in the benzene ring are illustrated below.

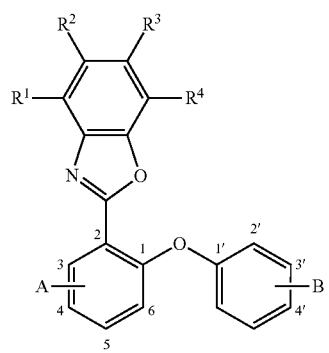

In the formula (2-1), $R^1$, $R^2$, $R^3$ and $R^4$ may be a branched alkyl group having 1 to 6 carbon atoms. Examples of the alkyl group include a methyl group, an ethyl group, a propyl group, an isopropyl group, a butyl group, a pentyl group, and a hexyl group. Among these, an alkyl group having 1 to 3 carbon atoms is preferable. Examples of the alkoxy group having 1 to 3 carbon atoms include a methoxy group, an ethoxy group, a propoxy group, an isopropoxy group. In particular, $R^1$, $R^2$, $R^3$ and $R^4$ are, independently of each other, a hydrogen atom or an alkyl group having 1 to 3 carbon atoms, further preferably a hydrogen atom.

The compound whose A and B in the formula (2-1) are both an amino group is represented by the formula (2-1-a) and is diamino-2-(benzoxazole-2-yl)diphenyl ether or its derivatives.

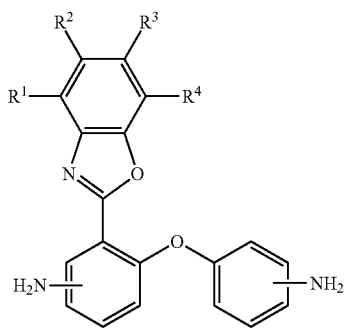

(2-1-a)

wherein $R^1$, $R^2$, $R^3$ and $R^4$ are as defined above.

The compound represented by the formula (2-1-a) is preferably one represented by the following formula.

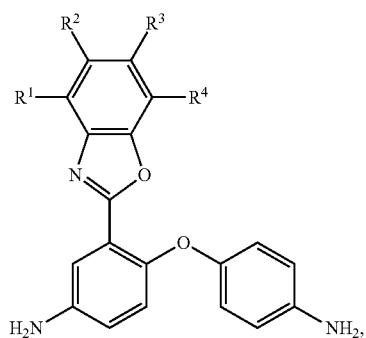

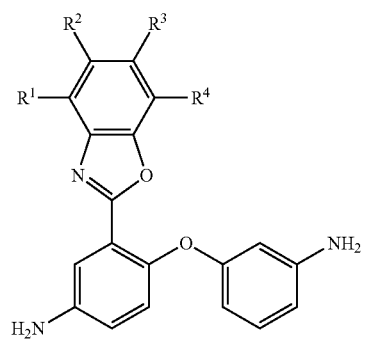

wherein $R^1$, $R^2$, $R^3$ and $R^4$ are as defined above, preferably are a 6 hydrogen atom or an alkyl group having 1 to 3 carbon atom, further a hydrogen atom.

The compound whose A and B in the formula (2-1) are both an nitro group is represented by the following formula (2-1-b) and is dinitro-2-(benzoxazole-2-yl)diphenyl ether and its derivatives. This compound may be used as an intermediate for the aforesaid diamino-2-(benzoxazole-2-yl) diphenyl ether or its derivatives, which are represented by the formula (2-1-a).

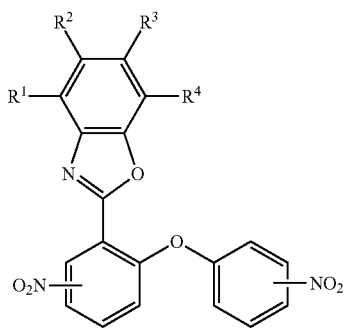

(2-1-b)

wherein $R^1$, $R^2$, $R^3$ and $R^4$ are as defined above.

The compound whose one of A and B in the formula (2-1) is an amino group and the other is an nitro group is represented by the following formula (2-1-c) or (2-1-d) and is aminonitro-2-(benzoxazole-2-yl)diphenyl ether or its derivatives. This compound may be used as an intermediate for the aforesaid diamino-2-(benzoxazole-2-yl)diphenyl ether or its derivatives, which are represented by the formula (2-1-a).

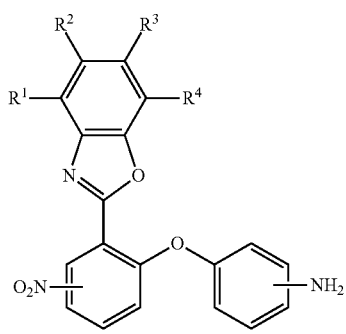

(2-1-c)

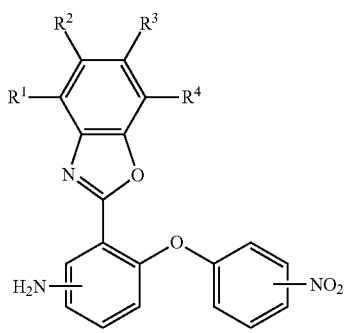

(2-1-d)

wherein $R^1$, $R^2$, $R^3$ and $R^4$ are as defined above.

The present compound 1 can be prepared by preparation method 1 as explained below.

[Preparation Method 1]

(1-1) Preparation of dinitro-2-(benzothiazole-2-yl) diphenyl ether or its derivatives (1-1-b) and amino-nitro-2-(benzothiazole-2-yl)diphenyl ether or its derivatives (1-1-c)

The compound represented by the aforesaid formula (1-1-b) or (1-1-c), hereinafter collectively represented by the following formula (1-1-e), is obtained by reacting a nitrophenyl benzothiazol compound such as 2-(2-chloro-5-nitrophenyl) benzothiazol with a phenol compound such as a 4-nitrophenol and 4-aminophenol or a metal salt thereof. The method is explained below in detail, and hereinafter referred to as preparation method 1-1.

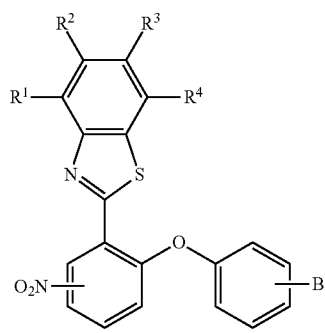
(1-1-e)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and B is a nitro group or an amino group.

(1-2) Preparation of aminonitro-2-(benzothiazole-2-yl)diphenyl ether and its derivatives (1-1-d)

The compound represented by the aforesaid formula (1-1-d) is obtained by reacting an aminophenyl benzothiazol compound such as 2-(2-chloro-5-aminophenyl) benzothiazol with a phenol compound such as a 4-nitrophenol or a metal salt thereof. The method is explained below in detail, and hereinafter referred to as preparation method 1-2.

(1-3) Preparation of diamino-2-(benzothiazole-2-yl) diphenyl ether and its derivatives (1-1-a)

The compound represented by the formula (1-1-a) is obtained by reacting an aminophenyl benzothiazol compound such as 2-(2-chloro-5-aminophenyl) benzothiazol with a phenol compound such as 4-aminophenol or a metal salt thereof. The method is explained below in detail, and hereinafter referred to as preparation method 1-2.

Meanwhile, the compound represented by the formula (1-1-a) is obtained by reducing a nitro group of the compound represented by the formula (1-1-b), (1-1-c) or (1-1-d). This method is explained below in detail, and hereinafter referred to as preparation method 1-3.

The preparation methods 1-1 to 1-3 are explained below in detail.

(1-1) Preparation Method 1-1

Preparation method 1-1 is for preparing the compound represented by the formula (1-1-e) which corresponds to the compound represented by the formula (1-e) wherein Q is a sulfur atom.

The compound represented by the formula (1-1-e) is obtained via etherification by reacting a nitrophenyl benzothiazol compound represented by the following formula (1-2):

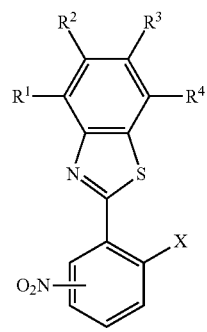
(1-2)

wherein $R^1$, $R^2$, $R^3$ and $R^4$ are as defined above and X is a halogen atom, with a phenol compound represented by the following formula (3) or a metal salt of the phenol compound:

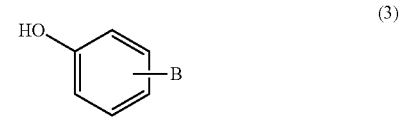
(3)

wherein B is a nitro group or an amino group.

Examples of the phenol represented by the formula (3) and its metal salt include 2-nitrophenol, 3-nitrophenol, 4-nitrophenol, 2-aminophenol, 3-aminophenol, 4-aminophenol, a 2-nitrophenol sodium salt, a 3-nitrophenol sodium salt, a 4-nitrophenol sodium salt, a 2-aminophenol sodium salt, a 3-aminophenol sodium salt, a 4-aminophenol sodium salt, a 2-nitrophenol potassium salt, a 3-nitrophenol potassium salt, a 4-nitrophenol potassium salt, a 2-aminophenol potassium salt, a 3-aminophenol potassium salt, a 4-aminophenol potassium salt, a 2-nitrophenol calcium salt, a 3-nitrophenol calcium salt, a 4-nitrophenol calcium salt, a 2-aminophenol calcium salt, a 3-aminophenol calcium salt, and a 4-aminophenol calcium salt.

The nitrophenyl benzothiazol compound represented by the formula (1-2) is obtained by amidation of an aminothiophenol compound represented by the following formula (1-a) such as 2-aminothiophenol with a nitrobenzoyl chloride compound represented by the following formula (b) such as 2-chloro-5-nitrobenzoyl chloride,

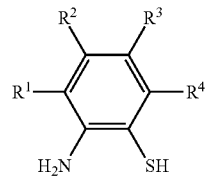
(1-a)

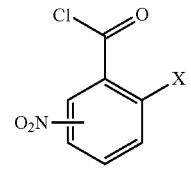
(b)

wherein R¹, R², R³ and R⁴ are as defined above and X is a halogen atom, followed by cyclization. Examples of the halogen atom include a chlorine atom, a bromine atom, and an iodine atom. In particular, a chlorine atom is preferable.

Examples of the aminothiophenol represented by formula (1-a) include 2-aminothiophenol, 3-methyl-2-aminothiophenol, 4-methyl-2-aminothiophenol, 5-methyl-2-aminothiophenol, 6-methyl-2-aminothiophenol, 3-ethyl-2-aminothiophenol, 4-ethyl-2-aminothiophenol, 5-ethyl-2-aminothiophenol, 6-ethyl-2-aminothiophenol, 3-propyl-2-aminothiophenol, 4-propyl-2-aminothiophenol, 5-propyl-2-aminothiophenol, 6-propyl-2-aminothiophenol, 3-isopropyl-2-aminothiophenol, 4-isopropyl-2-aminothiophenol, 5-isopropyl-2-aminothiophenol, 6-isopropyl-2-aminothiophenol, 3,4-dimethyl-2-aminothiophenol, 3,5-dimethyl-2-aminothiophenol, 3,6-dimethyl-2-aminothiophenol, 3,4,5-trimethyl-2-aminothiophenol, 3,4,6-trimethyl-2-aminothiophenol, 3,5,6-trimethyl-2-aminothiophenol, 3,4,5,6-tetramethyl-2-aminothiophenol, 3,4-diethyl-2-aminothiophenol, 3,5-diethyl-2-aminothiophenol, 3,6-diethyl-2-aminothiophenol, 3,4,5-triethyl-2-aminothiophenol, 3,4,6-triethyl-2-aminothiophenol, 3,5,6-triethyl-2-aminothiophenol, 3,4,5,6-tetraethyl-2-aminothiophenol, 3,4-dipropyl-2-aminothiophenol, 3,5-dipropyl-2-aminothiophenol, 3,6-dipropyl-2-aminothiophenol, 3,4,5-tripropyl-2-aminothiophenol, 3,4,6-tripropyl-2-aminothiophenol, 3,5,6-tripropyl-2-aminothiophenol, 3,4,5,6-tetrapropyl-2-aminothiophenol, 3,4-diisopropyl-2-aminothiophenol, 3,5-diisopropyl-2-aminothiophenol, 3,6-diisopropyl-2-aminothiophenol, 3,4,5-triisopropyl-2-aminothiophenol, 3,4,6-triisopropyl-2-aminothiophenol, 3,5,6-triisopropyl-2-aminothiophenol, and 3,4,5,6-tetraisopropyl-2-aminothiophenol.

Examples of the nitrobenzoyl chloride represented by formula (b) include 2-chloro-3-nitrobenzoyl chloride, 2-chloro-4-nitrobenzoyl chloride, 2-chloro-5-nitrobenzoyl chloride, 2-chloro-6-nitrobenzoyl chloride, 2-bromo-3-nitrobenzoyl chloride, 2-bromo-4-nitrobenzoyl chloride, 2-bromo-5-nitrobenzoyl chloride, 2-bromo-6-nitrobenzoyl chloride, 2-iodo-3-nitrobenzoyl chloride, 2-iodo-4-nitrobenzoyl chloride, 2-iodo-5-nitrobenzoyl chloride, and 2-iodo-6-nitrobenzoyl chloride.

(1-2) Preparation Method 1-2

Preparation method 1-2 is for preparing the compound represented by the formula (1-1-d) or the compound represented by the formula (1-1-a), hereinafter collectively represented by the following formula (1-1-f), which corresponds to the compound represented by the formula (1-f) wherein Q is a sulfur atom,

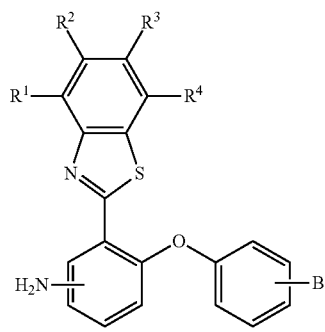

(1-1-f)

wherein R¹, R², R³ and R⁴ are as defined above and B is a nitro group or an amino group.

The compound represented by the formula (1-1-f) is obtained via etherification by reacting an aminophenyl benzothiazol compound represented by the following formula (1-4):

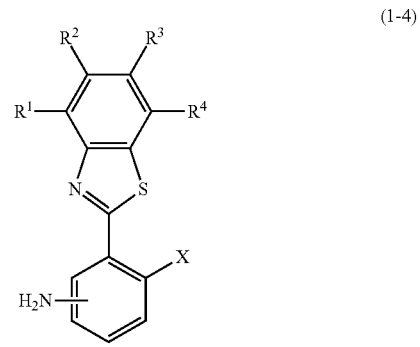

(1-4)

wherein R¹, R², R³ and R⁴ are as defined above and X is a halogen atom, with a phenol compound represented by the following formula (3) or a metal salt of the phenol compound:

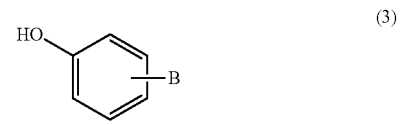

(3)

wherein B is a nitro group or an amino group.

Examples of the phenol compound represented by the formula (3) and the metal salt thereof are as described in preparation method (1-1).

The aminophenyl benzothiazol compound represented by the formula (1-4) is obtained by amidation of an aminothiophenol compound represented by the following formula (1-a) such as 2-aminothiophenol with an aminobenzoyl chloride compound represented by the following formula (c) such as 2-chloro-5-aminobenzoyl chloride,

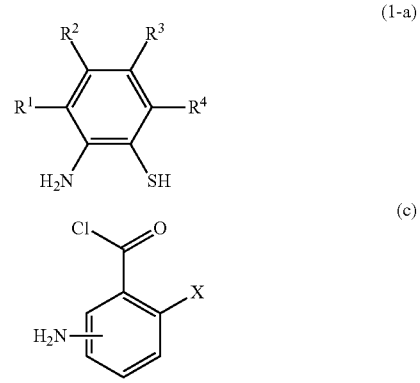

(1-a)

(c)

wherein R¹, R², R³ and R⁴ are as defined above and X is a halogen atom, followed by cyclization. Examples of the halogen atom include a chlorine atom, a bromine atom, and an iodine atom. In particular, a chlorine atom is preferable.

Examples of the aminobenzoyl chloride represented by the formula (c) include 2-chloro-3-aminobenzoyl chloride, 2-chloro-4-aminobenzoyl chloride, 2-chloro-5-aminobenzoylchloride, 2-chloro-6-aminobenzoylchloride, 2-bromo-3-aminobenzoyl chloride, 2-bromo-4-aminobenzoyl chloride, 2-bromo-5-aminobenzoyl chloride, 2-bromo-6-aminobenzoyl chloride, 2-iodo-3-aminobenzoyl chloride, 2-iodo-4-aminobenzoyl chloride, 2-iodo-5-aminobenzoyl chloride, and 2-iodo-6-aminobenzoyl chloride.

In the preparation methods 1-1 and 1-2, amounts of the compounds to be subjected to the amidation and the cyclization are such that a mole ratio of the benzoyl chloride represented by the formula (b) or (c) to the aminothiophenol represented by the formula (1-a) is preferably 0.8 to 1.5, further preferably 1 to 1.1.

In the preparation methods 1-1 and 1-2, the amidation and the cyclization may be conducted in the presence of a solvent. The kinds and the amount of the solvent may be selected properly as in known manners. For instance, an aprotic polar solvent may be used. Examples of the aprotic polar solvent include dimethylformamide, dimethylacetamide, N-methylpyrrolidone, N,N'-dimethylimidazolidinone, dimethylsulfoxide, sulfolane and hexamethylphosphoric triamide.

In the preparation methods 1-1 and 1-2, the cyclization may be conducted by using polyphosphoric acid as a dehydrating agent, or in the presence of an acid catalyst while removing formed water via azeotropy with toluene or xylene.

In the preparation methods 1-1 and 1-2, a reaction temperature and a period of time of the amidation and the cyclization may be selected properly as in known manners. For instance, the amidation may be carried out at 0 to 100 degrees C., preferably 0 to 50 degrees C., for 1 to 10 hours, preferably 2 to 5 hours. The cyclization may be carried out at 0 to 150 degrees C., preferably 30 to 100 degrees C., for 1 to 10 hours, preferably 2 to 5 hours. After-treatment of a resulting product is not limited. For instance, the reaction is stopped by dropwise adding methanol to the reaction solution, the solution is cooled, and a formed solid product is filtrated off, washed with water, and dried to obtain the compound represented by the formula (1-2) or (1-4).

In the preparation methods 1-1 and 1-2, the amount of the compounds to be subjected to the etherification is such that a mole ratio of the phenol compound represented by the formula (3) or a metal salt thereof to the benzothiazol compound represented by the formula (1-2) or (1-4) is preferably 0.8 to 1.3, further preferably 1.0 to 1.2.

In the preparation methods 1-1 and 1-2, the etherification may be conducted in the presence of a solvent. The solvent may be N-methylpyrrolidone. A reaction temperature and a period of time of the etherification may be selected properly. For instance, the etherification may be carried out at 100 to 200 degrees C., preferably 120 to 150 degrees C., for 0.5 to 10 hours, preferably 1 to 5 hours. After-treatment of a resulting product is not limited. For instance, the reaction is stopped by dropwise adding the reaction solution to methanol aqueous solution, the reaction solution is cooled, and a formed solid product is filtrated off, washed with water, dried and purified to obtain the compound represented by the formula (1-1-e) or (1-1-f).

(1-3) Preparation Method 1-3

Preparation method 1-3 is for preparing the compound represented by the formula (1-1-a) which corresponds to the compound represented by the formula (1-a) wherein Q is a sulfur atom.

The compound represented by the formula (1-1-a) is obtained by reducing a nitro group of the compound represented by the formula (1-1-b), (1-1-c) or (1-1-d). The compounds represented by the formula (1-1-b), (1-1-c) and (1-1-d) are prepared by the aforesaid preparation method 1-1 or 1-2. Accordingly, the preparation method 1-3 may be include a step for preparing the compound represented by the formula (1-1-b), (1-1-c) or (1-1-d) according to the preparation method 1-1 or 1-2.

The reduction reaction in the preparation 1-3 may be catalytic reduction, bechamp reduction, reduction with zinc powder, reduction with tin chloride and reduction with hydrazine. Catalytic reduction or reduction with hydrazine is preferred.

Examples of a solvent used in the reduction reaction include alcohols such as methanol, ethanol, 1-propanol, isopropanol, 1-butanol, 2-methoxyethanol and 2-ethoxyethanol; amides such as N,N-dimethylformamide, N,N-dimethylacetamide, N-methylpyrrolidone and N,N'-dimethylimidazolidinone; and ethers such as tetrahydrofuran, dioxane, ethylene glycol dimethyl ether, and diethylene glycol. The amount of the solvent may be properly adjusted.

Any known catalyst for reduction reactions may be used. For instance, examples of the catalyst used in the catalytic reduction or the reduction with hydrazine include novel metal catalysts such as palladium, platinum or rhodium supported on activated carbon, carbon black, graphite or alumina; raney nickel catalyst; and sponge nickel catalyst. The amount of the catalyst is generally 0.1 to 10 wt %, but is not limited.

A reaction temperature and a period of time of the reduction reaction may be properly selected. For instance, the reaction may be conducted at 50 to 150 degrees C., preferably 60 to 130 degrees C., for 1 to 10 hours, preferably 3 to 7 hours. After end of the reaction, for instance, the catalyst is removed, the reaction solution is cooled, and a resulting solid is filtrated off, washed with water and dried to thereby obtain the compound represented by the formula (1-1-a).

Compound 2 is obtained by the preparation method 2 as explained below.

[Preparation Method 2]

(2-1) Preparation of dinitro-2-(benzoxazole-2-yl) diphenyl ether and its derivatives (2-1-b) and aminonitro-2-(benzoxazole-2-yl)diphenyl ether and its derivatives (2-1-c)

The compound represented by the aforesaid formula (2-1-b) or (2-1-c), hereinafter collectively represented by the following formula (2-1-e), is obtained by reacting a nitrophenyl benzoxazole compound such as 2-(2-chloro-5-nitrophenyl)benzoxazole with a phenol compound such as 4-nitrophenol and 4-aminophenol or a metal salt thereof. The method is explained below in detail, hereinafter referred to as preparation method 2-1.

(2-1-e)

[Structure: benzoxazole with R1, R2, R3, R4 substituents, connected at 2-position to a phenyl group bearing O2N and an ether linkage to another phenyl group bearing B]

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and B is a nitro group or an amino group.

(2-2) Preparation of aminonitro-2-(benzoxazole-2-yl)diphenyl ether and its derivatives (2-1-d)

The compound represented by the aforesaid formula (2-1-d) is obtained by reacting an aminophenyl benzoxazole compound such as 2-(2-chloro-5-aminophenyl)benzoxazole with a phenol compound such as 4-nitrophenol or a metal salt thereof. The method is explained below in detail, hereinafter referred to as preparation method 2-2.

(2-3) Preparation of diamino-2-(benzoxazole-2-yl) diphenyl ether and its derivatives (2-1-a)

The compound represented by the formula (2-1-a) is obtained by reacting an aminophenyl benzoxazole compound such as 2-(2-chloro-5-aminophenyl)benzoxazole with a phenol compound such as 4-aminophenol or a metal salt thereof. The method is explained below in detail, hereinafter referred to as preparation method 2-2.

Meanwhile, the compound represented by the formula (2-1-a) is obtained by reducing a nitro group of the compound represented by the formula (2-1-b), (2-1-c) or (2-1-d). This method is explained below in detail, hereinafter referred to as preparation method 2-3.

The preparation methods 2-1 to 2-3 are explained below in detail.

(2-1) Preparation Method 2-1

Preparation method 2-1 is for preparing the compound represented by the formula (2-1-e) which corresponds to the compound represented by the formula (1-e) wherein Q is an oxygen atom.

The compound represented by the formula (2-1-e) is obtained via etherification by reacting a nitrophenyl benzoxazole compound represented by the following formula (2-2):

(2-2)

[Structure: benzoxazole with R1, R2, R3, R4 substituents, connected at 2-position to a phenyl group bearing O2N and X]

wherein $R^1$, $R^2$, $R^3$ and $R^4$ are as defined above and X is a halogen atom, with a phenol compound represented by the following formula (3) or a metal salt of the phenol compound:

(3)

[Structure: HO-phenyl-B]

wherein B is a nitro group or an amino group.

Examples of the phenol compound represented by the formula (3) and the metal salt thereof are as described in preparation method (1-1).

The nitrophenyl benzoxazole represented by the formula (2-2) is obtained by amidation of an aminophenol compound represented by the following formula (2-a) such as 2-aminophenol with a nitrobenzoyl chloride compound represented by the following formula (b) such as 2-chloro-5-nitrobenzoyl chloride, (2-a)

[Structure: benzene ring with R1, R2, R3, R4, H2N, and OH substituents]

(b)

[Structure: Cl-C(=O)- attached to phenyl ring bearing O2N and X]

wherein $R^1$, $R^2$, $R^3$ and $R^4$ are as defined above and X is a halogen atom, followed by cyclization. Examples of the halogen atom include a chlorine atom, a bromine atom, and an iodine atom. In particular, a chlorine atom is preferable.

Examples of the aminophenol represented by formula (2-a) include 2-aminophenol, 3-methyl-2-aminophenol, 4-methyl-2-aminophenol, 5-methyl-2-aminophenol, 6-methyl-2-aminophenol, 3-ethyl-2-aminophenol, 4-ethyl-2-aminophenol, 5-ethyl-2-aminophenol, 6-ethyl-2-aminophenol, 3-propyl-2-aminophenol, 4-propyl-2-aminophenol, 5-propyl-2-aminophenol, 6-propyl-2-aminophenol, 3-isopropyl-2-aminophenol, 4-isopropyl-2-aminophenol, 5-isopropyl-2-aminophenol, 6-isopropyl-2-aminophenol, 3,4-dimethyl-2-aminophenol, 3,5-dimethyl-2-aminophenol, 3,6-dimethyl-2-aminophenol, 3,4,5-trimethyl-2-aminophenol, 3,4,6-trimethyl-2-aminophenol, 3,5,6-trimethyl-2-aminophenol, 3,4,5,6-tetramethyl-2-aminophenol, 3,4-diethyl-2-aminophenol, 3,5-diethyl-2-aminophenol, 3,6-diethyl-2-aminophenol, 3,4,5-triethyl-2-aminophenol, 3,4,6-triethyl-2-aminophenol, 3,5,6-triethyl-2-aminophenol, 3,4,5,6-tetraethyl-2-aminophenol, 3,4-dipropyl-2-aminophenol, 3,5-dipropyl-2-aminophenol, 3,6-dipropyl-2-aminophenol, 3,4,5-tripropyl-2-aminophenol, 3,4,6-tripropyl-2-aminophenol, 3,5,6-tripropyl-2-aminophenol, 3,4,5,6-tetrapropyl-2-aminophenol, 3,4-diisopropyl-2-aminophenol, 3,5-diisopropyl-2-aminophenol, 3,6-diisopropyl-2-aminophenol, 3,4,5-triisopropyl-2-aminophenol, 3,4,6-triisopropyl-2-aminophenol, 3,5,6-triisopropyl-2-aminophenol, and 3,4,5,6-tetraisopropyl-2-aminophenol.

Examples of the nitrobenzoyl chloride represented by the formula (b) are as described in preparation method (1-1).

(2-2) Preparation Method 2-2

Preparation method 2-2 is for preparing the compound represented by the formula (2-1-d) or the compound represented by the formula (2-1-a), hereinafter collectively represented by the following formula (2-1-f), which corresponds to the compound represented by the formula (1-f) wherein Q is a oxygen atom.

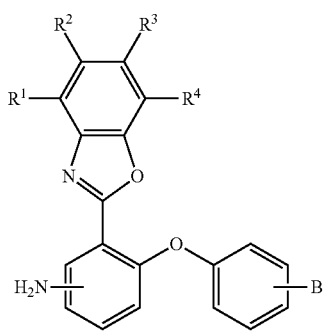

(2-1-f)

wherein $R^1$, $R^2$, $R^3$ and $R^4$ are as defined above and B is a nitro group or an amino group.

The compound represented by the formula (2-1-f) is obtained via etherification by reacting an aminophenyl benzoxazole compound represented by the following formula (2-4):

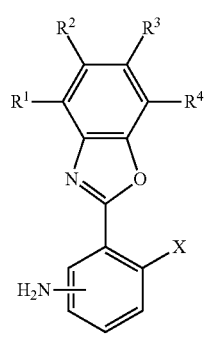

(2-4)

wherein $R^1$, $R^2$, $R^3$ and $R^4$ are as defined above and X is a halogen atom, with a phenol compound represented by the following formula (3) or a metal salt of the phenol compound:

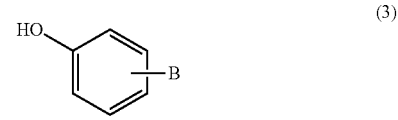

(3)

wherein B is a nitro group or an amino group.

Examples of the phenol compound represented by the formula (3) and the metal salt thereof are as described in preparation method (1-1).

The aminophenyl benzoxazole represented by the formula (2-4) is obtained by amidation of an aminophenol compound represented by the following formula (2-a), such as 2-aminophenol, with an aminobenzoyl chloride compound such as 2-chloro-5-aminobenzoyl chloride, represented by the following formula (c),

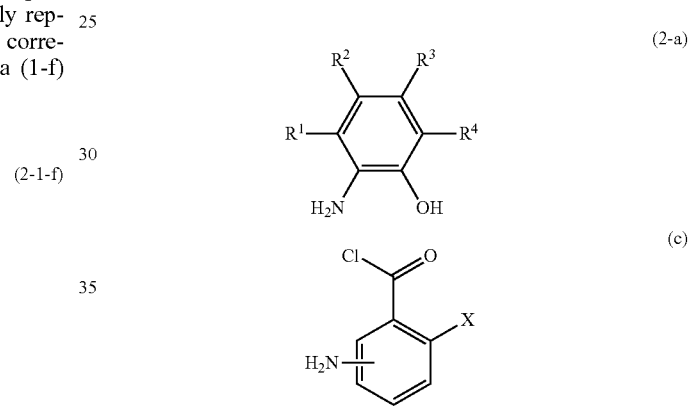

(2-a)

(c)

wherein $R^1$, $R^2$, $R^3$ and $R^4$ are as defined above and X is a halogen atom, followed by cyclization. Examples of the halogen atom include a chlorine atom, a bromine atom, and an iodine atom. In particular, a chlorine atom is preferable.

Examples of the aminobenzoyl chloride represented by the formula (c) are as described in preparation method (1-2).

In the preparation methods 2-1 and 2-2, the amounts of the compounds to be subjected to the amidation is such that a mole ratio of the of the benzoyl chloride compound represented by the formula (b) or (c) to the aminophenol compound represented by the formula (2-a) is preferably 1 to 1.5, further preferably 1 to 1.1.

In the preparation methods 2-1 and 2-2, the amidation and the cyclization may be conducted in the presence of a solvent. The kinds and the amount of the solvent may be selected properly as in known manners. For instance, an aprotic polar solvent may be used. Examples of the aprotic polar solvent include dimethylformamide, dimethylacetamide, N-methylpyrrolidone, N,N'-dimethylimidazolidinone, dimethylsulfoxide, sulfolane and hexamethylphosphoric triamide.

In the preparation methods 2-1 and 2-2, the cyclization may be conducted by using polyphosphoric acid as a dehydrating agent, or in the presence of an acid catalyst while removing formed water via azeotropy with toluene or xylene.

In the preparation methods 2-1 and 2-2, a reaction temperature and a period of time of the amidation and the cyclization may be selected properly as in known manners. For instance, the amidation may be carried out at 0 to 100 degrees C., preferably 0 to 50 degrees C., for 1 to 10 hours, preferably 2 to 5 hours. The cyclization may be carried out at 100 to 200 degrees C., preferably 50 to 150 degrees C., for 1 to 10 hours, preferably 2 to 5 hours. After-treatment of a resulting product is not limited. For instance, the reaction is stopped by dropwise adding methanol to the reaction solution, the reaction solution is cooled, and a formed solid product is filtrated off, washed with water, and dried to obtain the compound represented by the formula (2-2) or (2-4).

In the preparation methods 2-1 and 2-2, the amount of the compounds to be subjected to the etherification is such that a mole ratio of the phenol compound represented by the formula (3) or a metal salt thereof to the benzoxazole compound represented by the formula (2-2) or (2-4) is preferably 0.5 to 0.75, further preferably 0.5 to 0.6.

In the preparation methods 2-1 and 2-2, the etherification may be conducted in the presence of a solvent. The solvent may be dimethylsulfoxide. A reaction temperature and a period of time of the etherification may be selected properly. For instance, the etherification may be carried out at 50 to 200 degrees C., preferably 120 to 150 degrees C., for 1 to 10 hours, preferably 3 to 5 hours. After-treatment of a resulting product is not limited. For instance, the reaction is stopped by dropwise adding methanol to the reaction solution, the reaction solution is cooled, and a formed solid product is filtrated off, washed with water, dried and purified to obtain the compound represented by the formula (2-1-e) or (2-1-f).

(2-3) Preparation Method 2-3

Preparation method 2-3 is for preparing the compound represented by the formula (2-1-a) which corresponds to the compound represented by the formula (1-a) wherein Q is a oxygen atom.

The compound represented by the formula (2-1-a) is obtained by reducing a nitro group of the compound represented by the formula (2-1-b), (2-1-c) or (2-1-d). The compounds represented by the 26 formula. (2-1-b), (2-1-c) and (2-1-d) are prepared by the aforesaid preparation method 2-1 or 2-2. Accordingly, the preparation method 2-3 may be include a step for preparing the compound represented by the formula (2-1-b), (2-1-c) or (2-1-d) according to the preparation method 2-1 or 2-2.

The reduction reaction in the preparation 2-3 may be catalytic reduction, bechamp reduction, reduction with zinc powder, reduction with tin chloride and reduction with hydrazine. Catalytic reduction or reduction with hydrazine is preferred.

Examples of a solvent used in the reduction reaction include alcohols such as methanol, ethanol, 1-propanol, isopropanol, 1-butanol, 2-methoxyethanol and 2-ethoxyethanol; amides such as N,N-dimethylformamide, N,N-dimethylacetamide, N-methylpyrrolidone and N,N'-dimethylimidazolidinone; and ethers such as tetrahydrofuran, dioxane, ethylene glycol dimethyl ether, and diethylene glycol. The amount of the solvent may be properly adjusted.

Any known catalyst for reduction reactions may be used. For instance, examples of the catalyst used in the catalytic reduction and the reduction with hydrazine include novel metal catalysts such as palladium, platinum or rhodium supported on activated carbon, carbon black, graphite or alumina; raney nickel catalyst; and sponge nickel catalyst. The amount of the catalyst is generally 0.1 to 10 wt %, but is not limited.

A reaction temperature and a period of time of the reduction reaction may be properly selected. For instance, the reaction may be conducted at 50 to 150 degrees C., preferably 60 to 100 degrees C., for 1 to 10 hours, preferably 3 to 5 hours. After end of the reaction, for instance, the catalyst is removed, the reaction solution is cooled, and a resulting solid is filtrated off, washed with water and dried to thereby obtain the compound represented by the formula (2-1-a).

EXAMPLES

The present invention will be explained below in further detail with reference to a series of the Examples and the Comparative Examples, though the present invention is in no way limited by these Examples.

In the following descriptions, the HPLC determination was conducted by SPD-10A, ex Shimadzu Corporation, and the melting point was determined by MP-21, ex Yamato Scientific Co., Ltd.

Synthesis Example 1-1

Synthesis of 2-(2-chloro-5-nitrophenyl) benzothiazol

To 200-milliliter, four-neck flask equipped with a thermometer and an Allihn condenser, 8.1 g of 2-aminothiophenol and 40 g of N-methylpyrrolidone were added and dissolved. Then, 15.0 g of 2-chloro-5-nitrobenzoyl chloride dissolved in 25 g of N-methylpyrrolidone was added dropwise over 0.5 hour, while maintaining the internal temperature at 10 to 15 degrees C. After stirred for 2 hours, the temperature was raised to 50 degrees C. and maintained at this temperature for 3 hours. Then, 65 g of methanol was added dropwise. The reaction mixture was cooled to 35 degrees C., and the resulting solid was filtered off, washed with water and then dried to obtain 15.6 g of 2-(2-chloro-5-nitrophenyl) benzothiazol having a purity of 99.3%, as determined by HPLC, and a melting point of 189.0 to 190.5 degrees C.

Example 1-1

Synthesis of 2-(benzothiazole-2-yl)-4,4'-dinitrodiphenyl ether

To 100-milliliter, four-neck flask equipped with a thermometer and an Allihn condenser, 5.0 g of 2-(2-chloro-5-nitrophenyl) benzothiazol obtained in Synthesis Example 1-1, 3.8 g of sodium 4-nitrophenol having a purity of 97.8%, and 50 g of N-methylpyrrolidone were added and allowed to react for one hour at 120 to 125 degrees C. The reaction solution was added to 75 g of an aqueous 70% methanol solution. The resulting solid was filtered off, washed with water and then dried to obtain 6.2 g of a crude product, 2-(benzothiazole-2-yl)-4,4'-dinitrodiphenyl ether. A purity determined by HPLC was 98.9%. The crude product was decolorized with activated carbon and recrystallized from N-methylpyrrolidone to obtain 5.7 g of purified 2-(benzothiazole-2-yl)-4,4'-dinitrodiphenyl ether. A purity determined by HPLC was 99.4% and a melting point was 239.0 to 240.5 degrees C.

Example 1-2

Synthesis of 4,4'-diamino-2-(benzothiazole-2-yl)diphenyl ether

To 200-milliliter, four-neck flask equipped with a thermometer and an Allihn condenser, 3.0 g of 2-(benzothiazole- 2-yl)-4,4'-dinitrodiphenyl ether obtained in Example 1-1, 0.05 g of 5% Pd/C, and 100 g of 2-methoxyethanol were added. Then, 5.0 g of an aqueous solution of hydrazine was added dropwise over 0.5 hour at a reflux temperature and allowed to react for 6 hours. The catalyst was removed from the reaction solution, then, 50 g of 2-methoxy ethanol was distilled off, and the remaining materials were cooled to 30 degrees C. A resulting solid was filtered off, washed with water and then dried to obtain 2.3 g of pale lime green powder. A purity determined by HPLC was 99.6% and a melting point was 195.5 to 197.0 degrees C.

The product obtained was subjected to (i) $^1$H nuclear magnetic resonance spectrum analysis, (ii) $^{13}$C nuclear magnetic resonance spectrum analysis and (iii) mass analysis.

The $^1$H-NMR spectra and the $^{13}$C-NMR spectra were obtained with AVANCE400, ex Bruker Biospin, with a resonance frequency of 400 MHz. The solvent was dimethyl sulfoxide-d6.

Mass analysis was carried out with AXIMA Confidence, ex Shimadzu Corporation.

According to the following results, the solid product obtained was identified as 4,4'-diamino-2-(benzothiazole-2-yl)diphenyl ether.

(i) The $^1$H-NMR spectra were as described below. A chart of $^1$H-NMR spectra is shown in FIG. 1-1.

A singlet of a proton of an amino group was confirmed at delta 4.9 ppm (2H) and 5.2 ppm (2H); a doublet of a proton of the benzene nucleus was confirmed at delta 6.6 ppm (2H); a multiplet of a proton of the benzene nucleus and a proton of the benzene nucleus with the benzothiazole group was confirmed delta 6.7-6.8 ppm (4H); a triplet of a proton of the benzene nucleus with the benzothiazole group was confirmed at delta 7.7 ppm (1H); and a triplet, a triplet, a doublet and a doublet of the benzene nucleus of the benzothiazole group were confirmed at delta 7.4 ppm (1H), 7.5 ppm (1H), 8.0 ppm (1H) and 8.1 ppm (1H).

Figures 1, 2:
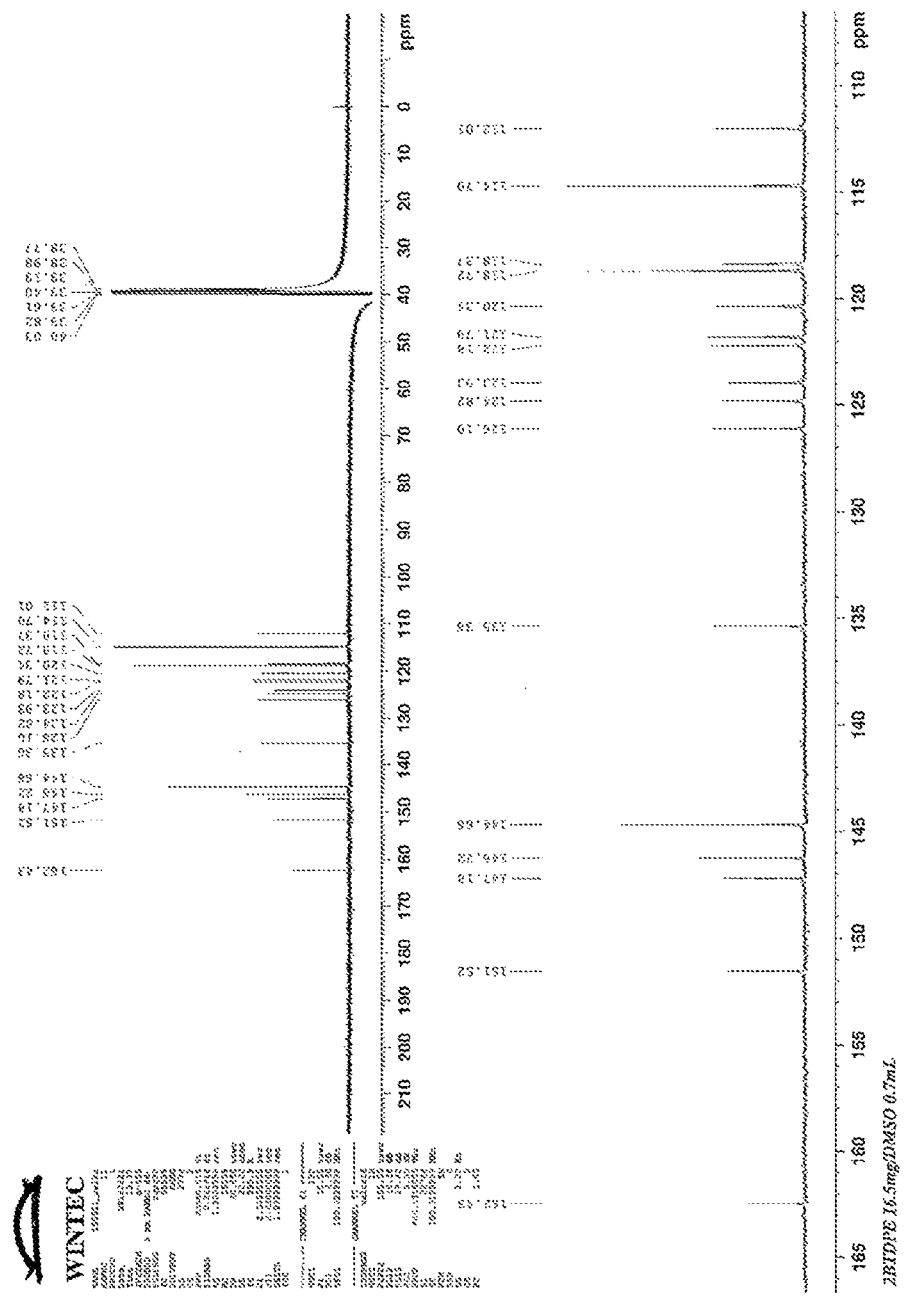

(ii) $^{13}$C nuclear magnetic resonance spectrum analysis showed 16 peaks. A chart of $^{13}$C-NMR spectra is shown in FIG. 1-2.

(iii) Mass analysis showed a main peak at 333.

Synthesis Example 2-1

Synthesis of 2-(2-chloro-5-nitrophenyl) benzoxazole

To one-liter, four-neck flask equipped with a thermometer and an Allihn condenser, 35.3 g of 2-aminophenol and 206 g of dimethyl sulfoxide were added and dissolved. Then, 75.0 g of 2-chloro-5-nitrobenzoyl chloride dissolved in 125 g of dimethyl sulfoxide was added dropwise over one hour while maintaining the internal temperature at 20 to 25 degrees C. After stirred for two hours, 54.4 g of polyphosphoric acid having a purity of 94.9% was added and allowed to react at 160 degrees C. for 3 hours. The reaction mixture was cooled to 70 degrees C., and 331 g of methanol was added dropwise. The remaining materials were cooled to 30 degrees C., and a resulting solid was filtered off, washed with water and then dried to obtain 79.3 g of 2-(2-chloro-5-nitrophenyl) benzoxazole. A purity determined by HPLC was 99.6% and a melting point was 169 to 170 degrees C.

Example 2-1

Synthesis of 2-(benzoxazole-2-yl)-4,4'-dinitrodiphenyl ether

To one-liter, four-neck flask equipped with a thermometer and an Allihn condenser, 79.0 g of 2-(2-chloro-5-nitrophenyl)benzoxazole obtained in Synthesis Example 2-1, 64.0 g of sodium 4-nitrophenol having a purity of 97.8%, and 700 g of dimethyl sulfoxide were added and allowed to react for one hour at 140 to 145 degrees C. The reaction solution was added to 1000 g of an aqueous 70% methanol solution. A resulting solid was filtered off, washed with water and then dried to obtain 99.4 g of a crude product, 2-(benzoxazole-2-yl)-4,4'-dinitrodiphenyl ether. A purity determined by HPLC was 99.2% and a melting point was 194 to 197 degrees C. The crude product was decolorized with activated carbon and recrystallized from N,N-dimethylformamide to obtain 94.4 g of purified 2-(benzoxazole-2-yl)-4,4'-dinitrodiphenyl ether. A purity determined by HPLC was 99.8% and a melting point was 195 to 196 degrees C.

Example 2-2

Synthesis of 4,4'-diamino-2-(benzoxazole-2-yl)diphenyl ether

To one-liter, four-neck flask equipped with a thermometer and an Allihn condenser, 30.0 g of 2-(benzoxazole-2-yl)-4,4'-dinitrodiphenyl ether obtained in Synthesis Example 2-1, 1.5 g of 5% Pd/C, and 700 g of isopropyl alcohol were added, then, 29.9 g of an aqueous solution of hydrazine was added dropwise over one hour at a reflux temperature and allowed to react for 4 hours. The catalyst was removed from the reaction solution, then, 500 g of isopropyl alcohol was distilled off, and the reaction solution was cooled to 30 degrees C. A resulting solid was filtered off, washed with water and then dried to obtain 23.3 g of yellow powder. A purity determined by HPLC was 99.2% and a melting point was 185 to 186 degrees C.

The product obtained was subjected to (i) $^1$H nuclear magnetic resonance spectrum analysis, (ii) $^{13}$C nuclear magnetic resonance spectrum analysis and (iii) mass analysis.

The $^1$H-NMR spectra was obtained with AVANCE400, ex Bruker Biospin, with a resonance frequency of 400 MHz. The solvent was acetone-d6.

The $^{13}$C-NMR spectra was obtained with JNM-ECA600, ex JEOL Ltd., with a resonance frequency of 600 MHz. The solvent was dimethyl sulfoxide-d6.

Mass analysis was carried out with AXIMA Confidence, ex Shimadzu Corporation.

According to the following results, the solid product obtained was identified as 4,4'-diamino-2-(benzoxazole-2-yl)diphenyl ether.

(i) The $^1$H-NMR spectra were as described below. A chart of $^1$H-NMR spectra is shown in FIG. 2-1.

A singlet of a proton of an amino group was confirmed at delta 4.4 ppm (2H) and 4.8 ppm (2H); a doublet of a proton of the benzene nucleus was confirmed at delta 6.6 ppm (2H) and 6.7 ppm (2H); a doublet, a quartet, a doublet of a proton of the benzene nucleus with the benzothiazole group was confirmed at delta 6.8 ppm (1H), 6.9 ppm (1H) and 7.5 ppm (1H); and a multiplet of a proton of the benzene nucleus of the benzoxazole group were confirmed at delta 7.3 ppm (2H), 7.6 ppm (1H) and 7.7 ppm (2H).

(ii) $^{13}$C nuclear magnetic resonance spectrum analysis showed 17 peaks. A chart of $^{13}$C-NMR spectra is shown in FIG. 2-2.

(iii) Mass analysis showed a main peak at 317.

Example 2-3

Synthesis of 2-(benzoxazole-2-yl)-3',4-dinitrodiphenyl ether

To 500-milliliter, four-neck flask equipped with a thermometer and an Allihn condenser, 70.0 g of 2-(2-chloro-5- nitrophenyl)benzoxazole obtained in Synthesis Example 2-1, 39.2 g of 4-nitrophenol, 15.4 g of sodium carbonate and 350 g of dimethyl sulfoxide were added and allowed to react at 105 to 110 degrees C. for 6 hours. The reaction solution was added to 150 g of an aqueous 75% methanol solution, and a resulting solid was filtered off, washed with water and then dried to obtain 94.0 g of a crude product, 2-(benzoxazole-2-yl)-3',4-dinitrodiphenyl ether. The crude product was decolorized with activated carbon and recrystallized from N,N-dimethylformamide to obtain 88.5 g of purified 2-(benzoxazole-2-yl)-3',4-dinitrodiphenyl ether. A purity determined by HPLC was 99.8% and a melting point was 214 to 215 degrees C.

Example 2-4

Synthesis of 3',4-diamino-2-(benzoxazole-2-yl)diphenyl ether

To two-liter, four-neck flask equipped with a thermometer, an Allihn condenser and a stirrer, 80.0 g of 2-(benzoxazole-2-yl)-3',4-dinitrodiphenyl ether obtained in Example 2-3, 4.0 g of 5% Pd/C (as wet), and 800 g of isopropyl alcohol were added and heated to a reflux temperature. Then, 80.0 g of an aqueous solution of hydrazine was added dropwise over one hour and allowed to react for 3 hours with maintaining the reflux temperature. The catalyst was removed from the reaction solution, then, 1600 g of an ion-exchange water was added, and the reaction solution was cooled to 30 degrees C. A resulting solid was filtered off, washed with water and then dried to obtain 56.2 g of lime green powder. A purity determined by HPLC was 99.9% and a melting point was 217 to 218 degrees C.

The product obtained was subjected to (i) $^1$H nuclear magnetic resonance spectrum analysis, (ii) $^{13}$C nuclear magnetic resonance spectrum analysis and (iii) mass analysis. Analysis equipments were as described in Example 2-2.

According to the following results, the solid product obtained was identified as 3',4-diamino-2-(benzoxazole-2-yl)diphenyl ether.

Figures 1, 2:
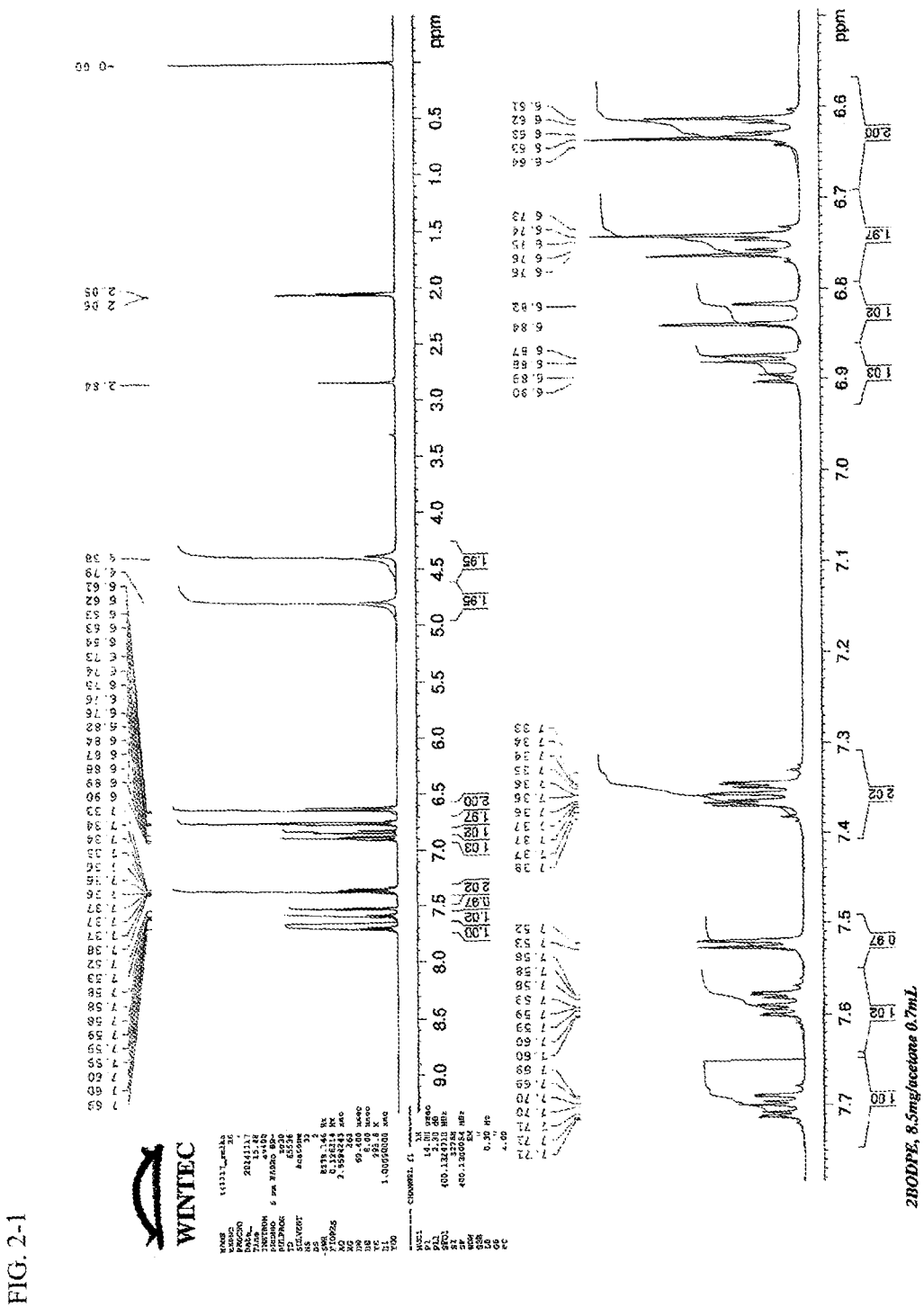
Figure 2:
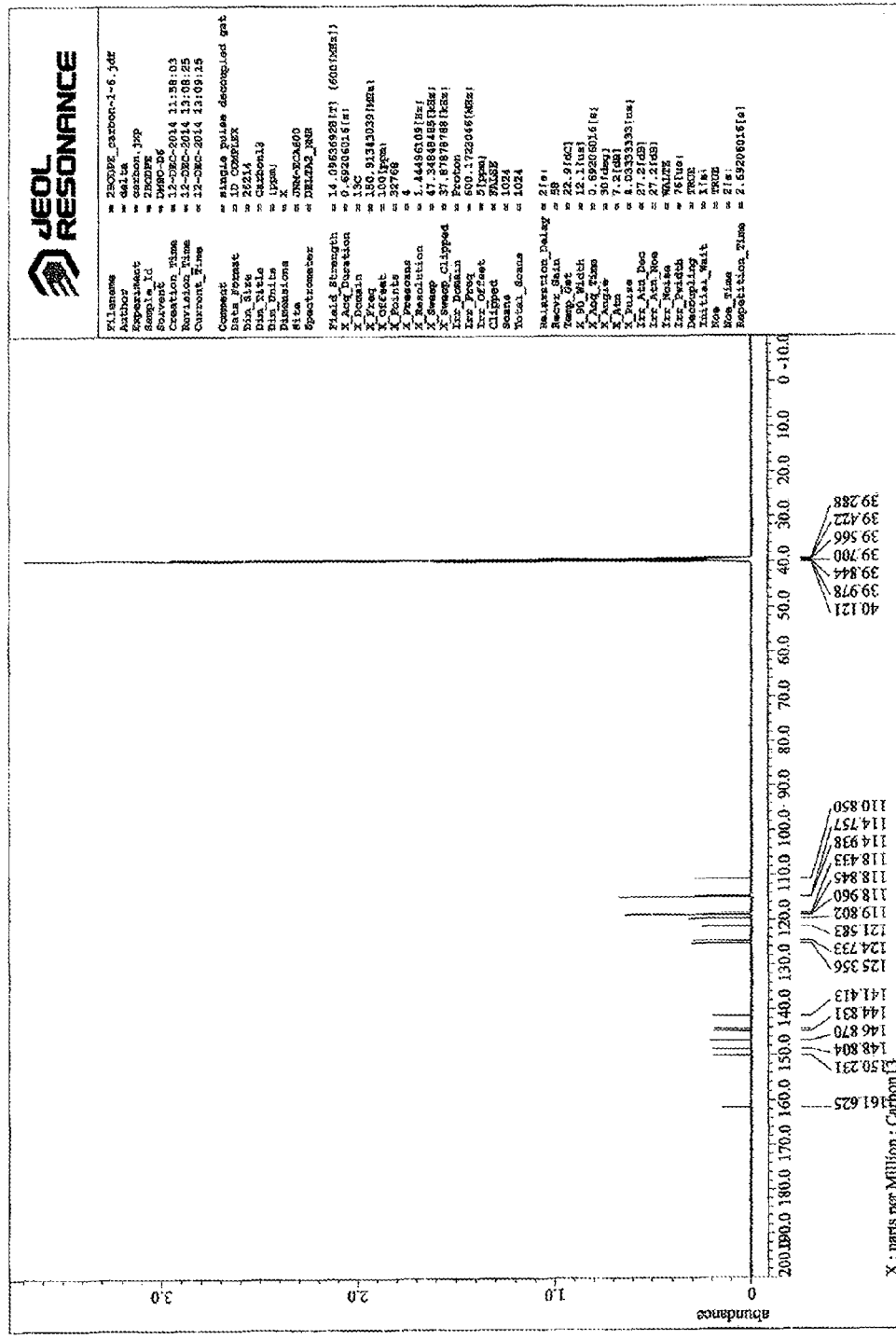
Figures 2, 3:
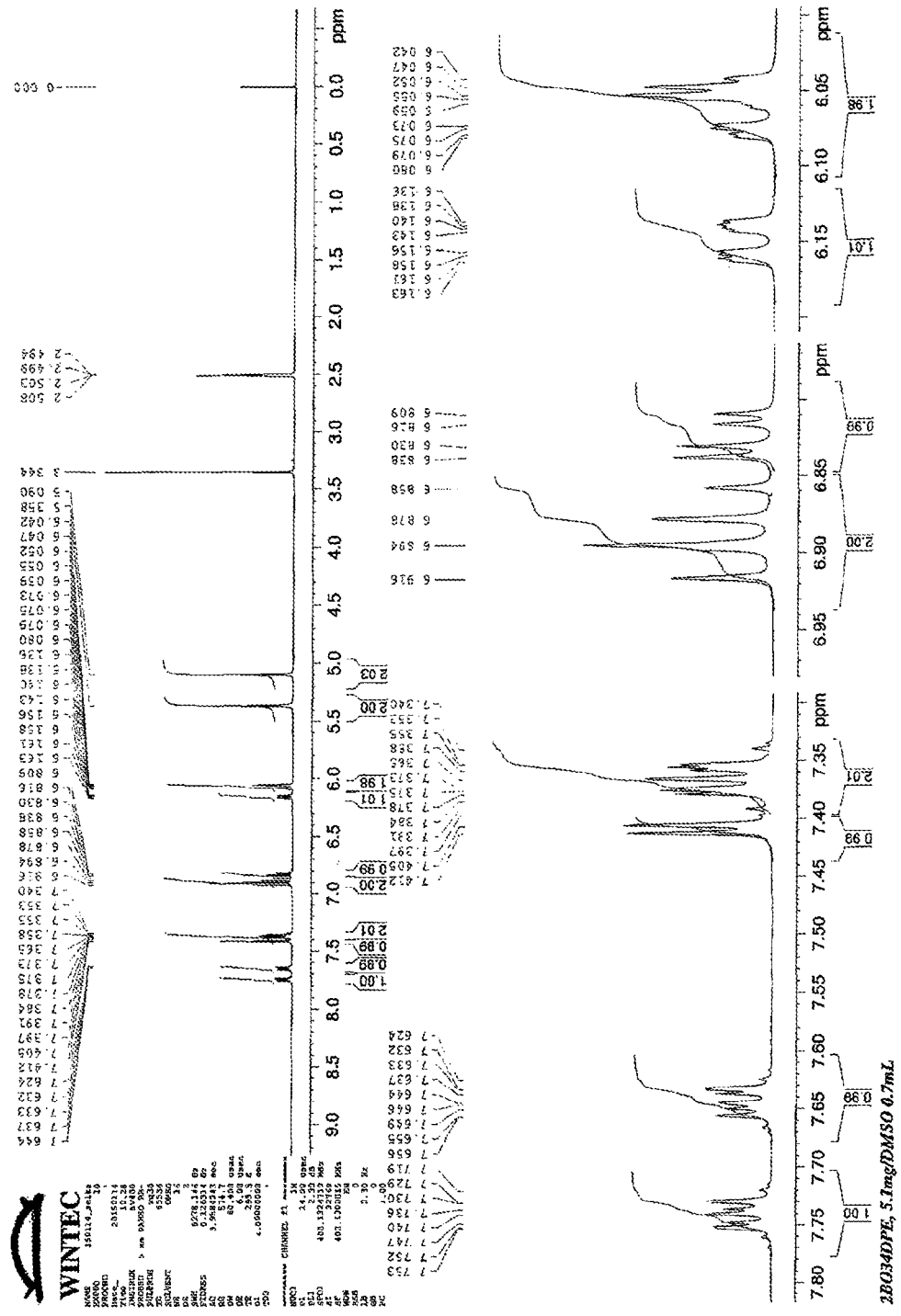

(i) The $^1$H-NMR spectra were as described below. A chart of $^1$H-NMR spectra is shown in FIG. 2-3. The solvent was dimethylsulfoxide-d6.

A singlet of a proton of an amino group was confirmed at delta 5.1 ppm (2H) and 5.4 ppm (2H); a multiplet, a multiplet, a multiplet and a quartet of a proton of the benzene nucleus were confirmed at delta 6.0 ppm (1H), 6.1 ppm (1H), 6.2 ppm (1H) and 6.8 ppm (1H); doublets of a proton of the benzene nucleus with the benzoxazole group were each confirmed at delta 6.8 ppm (1H), 6.9 ppm (1H) and 7.4 ppm (1H); and multiplets of a proton of the benzene nucleus of the benzoxazole group were each confirmed at delta 7.3 to 7.4 ppm (2H), 7.6 ppm (1H) and 7.7 ppm (1H).

Figures 2, 3, 4:
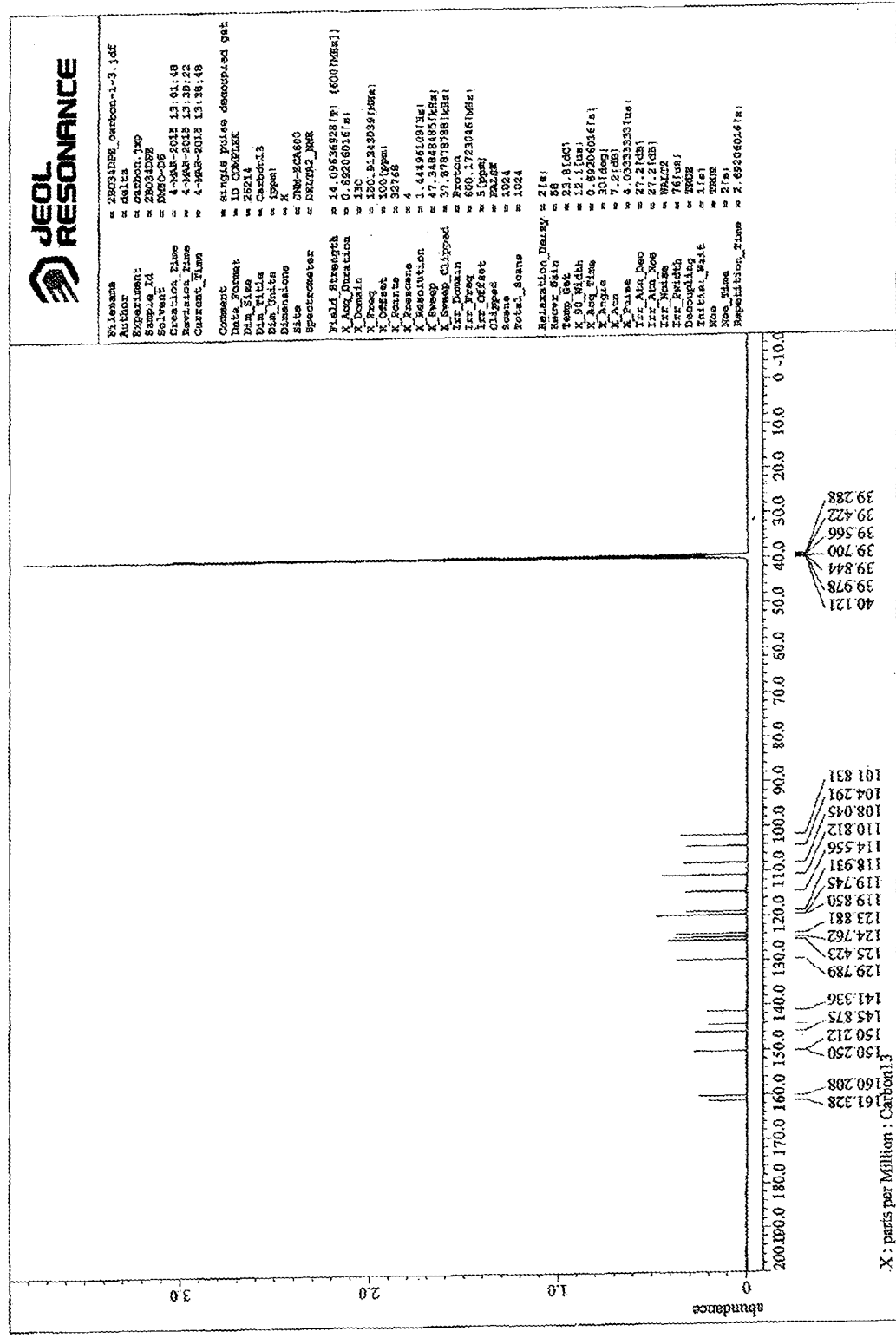

(ii) $^{13}$C nuclear magnetic resonance spectrum analysis showed 19 peaks. The solvent was dimethylsulfoxide-d6. A chart of $^{13}$C-NMR spectra is shown in FIG. 2-4.

(iii) Mass analysis showed a main peak at 317.

INDUSTRIAL APPLICABILITY

Diamino-2-(benzothiazole-2-yl)diphenyl ether and its derivatives, and diamino-2-(benzoxazole-2-yl)diphenyl ether and its derivatives are suitably used as an asymmetric diamine, broaden the potentiality of the field of polyimides derived from the compounds and provide new functional materials. Dinitro-2-(benzothiazole-2-yl)diphenyl ether, aminonitro-2-(benzothiazole-2-yl)diphenyl ether, and derivatives thereof are usable as an intermediate for diamino-2-(benzothiazole-2-yl)diphenyl ether and derivatives thereof. Dinitro-2-(benzoxazole-2-yl)diphenyl ether, aminonitro-2-(benzoxazole-2-yl) diphenyl ether, and derivatives thereof are usable as an intermediate for diamino-2-(benzoxazole-2-yl)diphenyl ether and derivatives thereof. These intermediates also broaden the potentiality of the field of polyimides.

The invention claimed is:

1. A compound represented by the following formula (1):

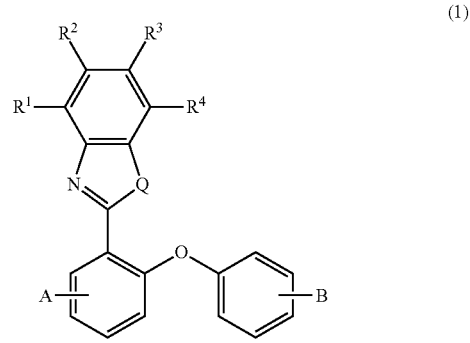

(1)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, A and B are, independently of each other, a nitro group or an amino group, and Q is an oxygen atom or a sulfur atom.

2. The compound according to claim 1, wherein A and B are both an amino group.

3. A method for preparing a compound represented by the following formula (1-e):

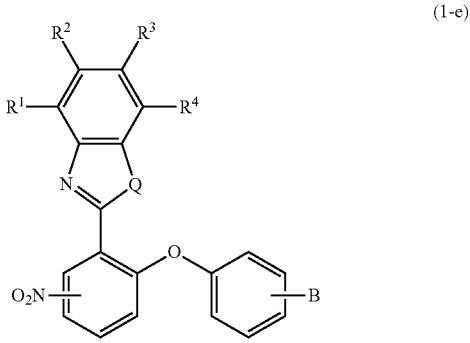

(1-e)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, B is a nitro group or an amino group, and Q is an oxygen atom or a sulfur atom, wherein the method comprises a step of reacting a nitrophenyl benzothiazole or nitrophenyl benzoxazole compound represented by the following formula (2):

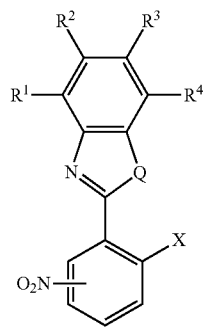

(2)

wherein Q, $R^1$, $R^2$, $R^3$ and $R^4$ are as defined above and X is a halogen atom, with a phenol compound represented by the following formula (3) or a metal salt of said phenol compound:

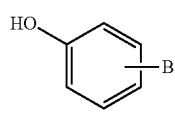

(3)

wherein B is a nitro group or an amino group, to thereby prepare the compound represented by the aforesaid formula (1-e).

4. A method for preparing a compound represented by the following formula (1-f):

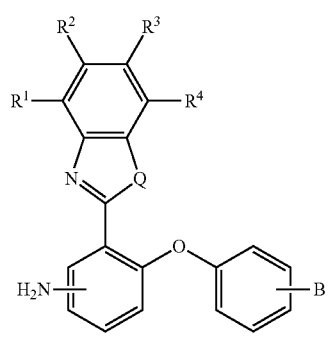

(1-f)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, B is a nitro group or an amino group, and Q is an oxygen atom or a sulfur atom, wherein the method comprises a step of reacting an aminophenyl benzothiazole or aminophenyl benzoxazole compound represented by the following formula (4):

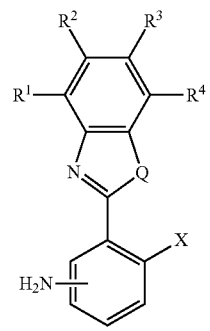

(4)

wherein Q, $R^1$, $R^2$, $R^3$ and $R^4$ are as defined above and X is a halogen atom, with a phenol compound represented by the following formula (3) or a metal salt of said phenol compound:

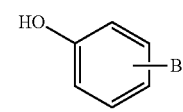

(3)

wherein B is a nitro group or an amino group, to thereby prepare the compound represented by the aforesaid formula (1-f).

5. A method for preparing a compound represented by the following formula (1-a):

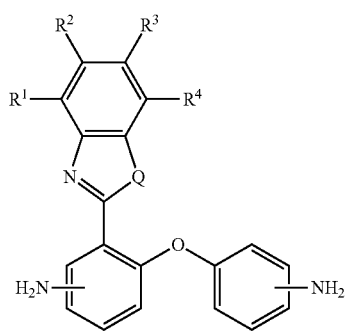

(1-a)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and Q is an oxygen atom or a sulfur atom, wherein the method comprises a step of reducing a nitro group of a compound represented by the following formula (1-e) or (1-d) to thereby prepare the compound represented by the aforesaid formula (1-a),

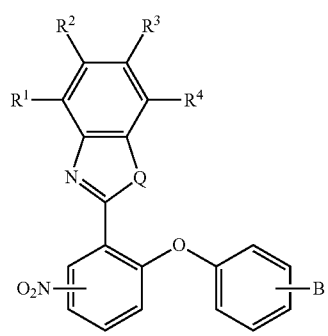

(1-e)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, B is a nitro group or an amino group, and Q is an oxygen atom or a sulfur atom,

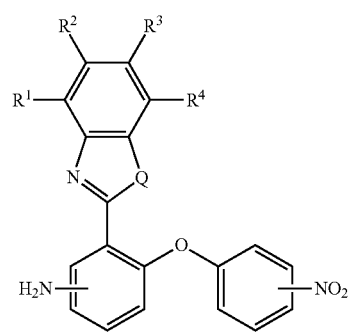

(1-d)

wherein $R^1$, $R^2$, $R^3$ and $R^4$ are, independently of each other, a hydrogen atom, an alkyl group having 1 to 6 carbon atoms, or an alkoxy group having 1 to 3 carbon atoms, and Q is an oxygen atom or a sulfur atom.

* * * * *